United States Patent
Mahajan et al.

(10) Patent No.: US 11,806,543 B2
(45) Date of Patent: Nov. 7, 2023

(54) SUPERVISED CARDIAC EVENT DETECTION

(71) Applicant: Cardiac Pacemakers, Inc., St. Paul, MN (US)

(72) Inventors: Deepa Mahajan, North Oaks, MN (US); David L. Perschbacher, Coon Rapids, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 152 days.

(21) Appl. No.: 16/460,569

(22) Filed: Jul. 2, 2019

(65) Prior Publication Data

US 2020/0016420 A1    Jan. 16, 2020

Related U.S. Application Data

(60) Provisional application No. 62/696,499, filed on Jul. 11, 2018.

(51) Int. Cl.
  *A61N 1/39*  (2006.01)
  *A61B 5/00*  (2006.01)
  (Continued)

(52) U.S. Cl.
  CPC .......... *A61N 1/3925* (2013.01); *A61B 5/363* (2021.01); *A61B 5/6805* (2013.01);
  (Continued)

(58) Field of Classification Search
  CPC .. A61N 1/3925; A61N 1/3956; A61N 1/3993; A61B 5/363; A61B 5/6805;
  (Continued)

(56) References Cited

U.S. PATENT DOCUMENTS

| 9,533,165 B1 * | 1/2017 | Gunderson .......... A61N 1/3931 |
| 2011/0112597 A1 * | 5/2011 | Snell .................... A61B 5/0452 607/27 |

(Continued)

FOREIGN PATENT DOCUMENTS

| CN | 112469335 A | 3/2021 |
| WO | WO-2020014045 A1 | 1/2020 |

OTHER PUBLICATIONS

Zou et. al., "Receiver-Operating Characteristic Analysis for Evaluating Diagnostic Tests and Predictive Models". Feb. 6, 2007. Circulation. 2007;115:654-657.*

(Continued)

*Primary Examiner* — Lynsey C Eiseman
*Assistant Examiner* — Ranjani Mari Sundaresan
(74) *Attorney, Agent, or Firm* — Schwegman Lundberg & Woessner, P.A.

(57) ABSTRACT

Systems and methods for detecting physiologic events in a patient are described herein. An embodiment of a medical system includes a memory circuit to store physiologic event episodes detected and recorded by a medical device. The system includes a control circuit to analyze the stored physiologic event episodes, and determine a presence of a target cardiac event under a plurality of detection settings. Using the determined presence of the target cardiac event from the stored physiologic event episodes, and user adjudication of the stored event episodes, the control circuit may select, from the plurality of detection settings, a detection setting to detect a subsequent target cardiac event. The control circuit may also prioritize the physiologic event episodes for storage in the memory circuit.

20 Claims, 7 Drawing Sheets

(51) Int. Cl.
*A61B 5/363* (2021.01)
*A61B 5/364* (2021.01)

(52) U.S. Cl.
CPC ............ *A61B 5/7282* (2013.01); *A61B 5/746* (2013.01); *A61N 1/3956* (2013.01); *A61B 5/364* (2021.01); *A61B 5/7221* (2013.01); *A61N 1/3993* (2013.01)

(58) Field of Classification Search
CPC ....... A61B 5/7282; A61B 5/746; A61B 5/364; A61B 5/7221; A61B 5/349; A61B 5/316
See application file for complete search history.

(56) References Cited

U.S. PATENT DOCUMENTS

| 2015/0342466 | A1 | 12/2015 | Thakur et al. |
| 2017/0027462 | A1 | 2/2017 | Mahajan et al. |
| 2017/0231505 | A1 | 8/2017 | Mahajan et al. |
| 2017/0290550 | A1* | 10/2017 | Perschbacher ....... A61B 5/4836 |
| 2018/0028086 | A1 | 2/2018 | Cao et al. |

OTHER PUBLICATIONS

Cho MS, Kim J, Kim JH, Kim M, Lee JH, et al. (2016) Clinical, Echocardiographic, and Electrocardiographic Predictors of Persistent Atrial Fibrillation after Dual-Chamber Pacemaker Implantation: An Integrated Scoring Model Approach. PLOS ONE 11(8): e0160422.*

Hu et al, Predictive combinations of monitor alarms preceding in-hospital code blue events, Journal of Biomedical Informatics, vol. 45, Issue 5, 2012, pp. 913-921. (Year: 2012).*

Passman et al, Development and validation of a dual sensing scheme to improve accuracy of bradycardia and pause detection in an insertable cardiac monitor, Heart Rhythm, vol. 14, Issue 7, 2017, pp. 1016-1023, ISSN 1547-5271 (Year: 2017).*

"International Application Serial No. PCT/US2019/040338, International Preliminary Report on Patentability dated Jan. 21, 2021", 8 pgs.

"International Application Serial No. PCT/US2019/040338, International Search Report dated Oct. 25, 2019", 5 pgs.

"International Application Serial No. PCT/US2019/040338, Written Opinion dated Oct. 25, 2019", 6 pgs.

* cited by examiner

SUPERVISED CARDIAC EVENT DETECTION

CLAIM OF PRIORITY

This application claims the benefit of priority under 35 U.S.C. § 119(e) of U.S. Provisional Patent Application Ser. No. 62/696,499, filed on Jul. 11, 2018, which is herein incorporated by reference in its entirety.

TECHNICAL FIELD

This document relates generally to medical devices, and more particularly, to systems, devices and methods for detecting cardiac events the detected cardiac event episodes.

BACKGROUND

Implantable medical devices (IMDs) have been used for monitoring patient health condition or disease states and delivering therapies. For example, implantable cardioverter-defibrillators (ICDs) are used to monitor certain abnormal heart rhythms. Some IMDs may be used to monitor progression of a chronic disease, such as worsening of cardiac performance due to congestive heart failure (CHF). In addition to diagnostic capabilities, the IMDs may also provide therapies to treat or alleviate certain medical conditions, such as cardiac electrostimulation therapies to treat cardiac arrhythmia or to rectify cardiac dyssynchrony in CHF patients.

The IMDs may record medical data associated with detected physiologic events such as a cardiac arrhythmia or worsening heart failure (WHF). Some IMDs may register a patient-triggered episode of a physiologic event, and record physiologic data in response to the patient trigger. The IMDs may be interconnected to a patient management system via a data communication network. Device data, such as the medical data associated with the detected physiologic events, may be transmitted to a patient management system, through which a healthcare professional may remotely follow up with the patients or assess functions of the IMDs on a regular basis. For example, the healthcare provider may review the recorded medical data associated with physiologic event episodes, determine the presence of or possible causes leading to the physiologic event, or assess whether a prescribed therapy has resulted in the desired therapeutic outcome.

OVERVIEW

An ambulatory medical device (AMD) may detect cardiac events (e.g., cardiac arrhythmias) using a programmable detection setting, such as detection parameters and the associated sensitivity levels. The AMD may record physiologic event episodes upon detection of the cardiac event. The physiologic event episodes may be managed using a patient management system. For example, the patient management system may frequently receive alert notifications on the cardiac events, such as cardiac arrhythmia or worsening heart failure (WHF) events detected by the AMD. A user (e.g., a clinician) may review the physiologic event episodes, make annotations, schedule patient follow-up visits, or reprogram the AMDs, among other operations.

The patient management system may concurrently manage physiologic event episodes from multiple AMDs. Human review and annotation of a large amount of device-detected physiologic event data, such as cardiac arrhythmia episodes, may require substantial clinical, technical, and human resources, which can be costly or otherwise time consuming for a healthcare facility. Some alert notifications are due to repeated false positive detections of cardiac events by the AMDs. The false positive detection may have the same or similar underlying causes. The FP detections may inappropriately trigger therapies (e.g., arrhythmia therapies delivered by the AMD) or other medical interventions. Additionally, the FP detections may repeatedly trigger alert notifications, demanding medical attention or episode review and annotation. To prevent or reduce repeated FP detections, particularly those with the same or similar underlying causes, the cardiac event detection settings in the AMD need to be properly and timely adjusted. The present inventors have recognized an unmet need for physiologic event detection and medical alert management, particularly a need for improved systems and methods to automatically learn from patient previous FP detections, adjust the detection settings, and improve AMD function.

This document discusses, among other things, systems, devices, and methods for detecting physiologic events in a patient. An embodiment of a medical system includes a memory circuit to store physiologic event episodes, such as recorded by an ambulatory medical device. The medical system includes a control circuit to perform simulations on the stored physiologic event episodes to determine a presence of a target cardiac event under different detection settings. The control circuit may provide the determined presence of the target cardiac event under a first detection setting to a user (e.g., a clinician), and receive from the user an adjudication of the provided determination of the presence of the target cardiac event under a first detection setting. The control circuit may re-determine a presence of the target cardiac event in the stored physiologic event episodes under a second detection setting different the first detection setting, and provide the re-determined presence of the target cardiac event under the second detecting setting to the user. The control circuit may compare the determinations of the presence of the target cardiac event under the first and second detection settings, and present the comparison to the user, such as on a display unit. Based on the comparison, the user may make a selection between the first and second detection settings. The control circuit may receive this user selection to detect a subsequent target cardiac event. The control circuit may prioritize the physiologic event episodes for storage in the memory circuit.

Example 1 is a system for detecting cardiac events from a patient. The system comprises a memory circuit and a control circuit. The memory circuit is configured to store physiologic event episodes recorded by a medical device from a patient. The control circuit includes a detection control circuit that is configured to: determine a presence of a target cardiac event in one or more of the stored physiologic event episodes under a first detection setting; provide the determined presence of the target cardiac event under the first detection setting to a user; receive from the user an adjudication of the provided determined presence of the target cardiac event under the first detection setting; re-determine a presence of the target cardiac event in the one or more of the stored physiologic event episodes under a second detection setting different than the first detection setting; provide the re-determined presence of the target cardiac event in the one or more stored physiologic event episodes under the second detecting setting to the user; and receive, in response to the provided re-determined presence of the target cardiac event, a selected detection setting for a subsequent determination of the presence of the target cardiac event in the patient.

In Example 2, the subject matter of Example 1 optionally includes the detection control circuit that may be configured to determine a first false positive (FP) detection count corresponding to the first detection setting, and a second FP detection count corresponding to the second detection setting, and to provide the determined first and second FP detection counts to the user.

In Example 3, the subject matter of any one or more of Examples 1-2 optionally includes the detection control circuit that may be configured to determine a receiver operating characteristic (ROC) with operating points including the first and second detection settings, and to provide the determined ROC to the user.

In Example 4, the subject matter of any one or more of Examples 1-3 optionally includes the first and second detection settings that may include respective first and second sensitivity levels. To determine the presence of the target cardiac event in one of the stored physiologic event episodes, the detection control circuit may be configured to compare a physiologic parameter derived from the one of the stored physiologic event episodes to the first and second sensitivity levels.

In Example 5, the subject matter of Example 4 optionally includes the first and second sensitivity levels each representing thresholds or value ranges of the physiologic parameter.

In Example 6, the subject matter of any one or more of Examples 4-5 optionally includes the target cardiac event that may include atrial tachyarrhythmia, and the plurality of sensitivity levels may include thresholds or value ranges of at least one of: a heart rate; a heart rate stability; an electrogram morphology measurement; or a cardiac contractility measurement.

In Example 7, the subject matter of any one or more of Examples 4-6 optionally includes the detection control circuit that may be configured to determine, for each of the stored physiologic event episodes, a lowest sensitivity level ($Sens_{LST}$) among the plurality of sensitivity levels that are capable of detecting the presence of the target cardiac event from the corresponding stored physiologic event episode, and to select the detection setting further using the $Sens_{LST}$ of the stored physiologic event episodes.

In Example 8, the subject matter of Example 7 optionally includes the control circuit that may further include a storage control circuit configured to prioritize the stored physiologic event episodes based on the $Sens_{LST}$ of the stored physiologic event episodes.

In Example 9, the subject matter of Example 8 optionally includes the storage control circuit that may be configured to assign a higher priority to an event episode if the $Sens_{LST}$ falls below a sensitivity level threshold, and to assign a lower priority to an event episode if the $Sens_{LST}$ exceeds the sensitivity level threshold.

In Example 10, the subject matter of Example 9 optionally includes the storage control circuit that may be configured to store a first number of data features of the event episode if a high priority is assigned, and to store a second, lower number of data features of the event episode if a low priority is assigned.

In Example 11, the subject matter of any one or more of Examples 1-10 optionally includes the first and second detection settings that may include respective first and second duration thresholds. To determine the presence of the target cardiac event in one of the stored physiologic event episodes, the detection control circuit may be configured to compare a duration of the one of the stored physiologic event episodes to the first and second duration thresholds.

In Example 12, the subject matter of any one or more of Examples 1-11 optionally includes a user interface configured to receive a user input of the adjudication of the stored physiologic event episodes, and the control circuit may be configured to program the selected detection setting for the subsequent determination of the presence of the target cardiac event in the patient.

In Example 13, the subject matter of Example 12 optionally includes the user interface that may be configured to display an indication of the presence of the target cardiac event in the stored physiologic event episodes under the first and second detection settings.

In Example 14, the subject matter of any one or more of Examples 1-13 optionally includes an ambulatory medical device (AMD) configured to detect a target cardiac event from a subsequent patient physiologic event episode using the received selection of detection setting.

In Example 15, the subject matter of any of claims 1-14 optionally includes the control circuit that may be configured to automatically select between the first and second detection settings for detecting a subsequent target cardiac event, and the selection may be based on the determined presence of a target cardiac event in each of the stored physiologic event episodes under the first and second detection settings. Example 16 is a method for detecting cardiac events. The method comprises steps of: determining, using a control circuit, a presence of a target cardiac event in one or more stored physiologic event episodes stored in a memory under a first detection setting; providing the determined presence of the target cardiac event under the first detection setting to a user; receiving an adjudication of the provided determined presence of the target; re-determining, using the control circuit, a presence of the target cardiac event in the one or more of the stored physiologic event episodes under a second detection setting different than the first detection setting; providing the re-determined presence of the target cardiac event in the one or more stored physiologic event episodes under the second detecting setting to the user; and receiving, in response to the provided re-determined presence of the target cardiac event, a selected detection setting for a subsequent determination of the presence of the target cardiac event in the patient.

In Example 17, the subject matter of Example 16 optionally includes determining a first false positive (FP) detection count corresponding to the first detection setting, and a second FP detection count corresponding to the second detection setting, and providing the determined first and second FP detection counts to the user.

In Example 18, the subject matter of any one or more of Examples 16-17 optionally includes determining a receiver operating characteristic (ROC) with operating points including the first and second detection settings, and providing the determined ROC to the user.

In Example 19, the subject matter of any one or more of Examples 16-18 optionally includes the first and second detection settings that may include respective first and second sensitivity levels. The determination of the presence of the target cardiac event in a stored physiologic event episode includes using a comparison of a physiologic parameter derived from the stored physiologic event episode to the first and second sensitivity levels.

In Example 20, the subject matter of Example 19 optionally includes determining, for each of the stored physiologic event episodes, a lowest sensitivity level ($Sens_{LST}$) among a plurality of sensitivity levels including the first and second sensitivity levels that are capable of detecting the presence of the target cardiac event from the corresponding stored physiologic event episode, and selecting a detection setting from the plurality of sensitivity levels using the $\text{Sens}_{LST}$ of the stored physiologic event episodes.

In Example 21, the subject matter of Example 20 optionally includes prioritizing the stored physiologic event episodes based on the $\text{Sens}_{LST}$ of the stored physiologic event episodes using a storage control circuit.

In Example 22, the subject matter of any one or more of Examples 16-21 optionally includes the first and second detection settings that may include respective first and second duration thresholds, and the determination of the presence of the target cardiac event in a stored physiologic event episode includes using a comparison of a duration of the stored physiologic event episode to the first and second duration thresholds.

In Example 23, the subject matter of any one or more of Examples 16-22 optionally includes detecting a target cardiac event from a subsequent patient physiologic event episode using an ambulatory medical device at the selected detection setting.

Example 24 is a method for detecting cardiac events. The method comprises steps of: displaying on a user interface one or more first cardiac events detected in physiological episode using a detection algorithm having a first detection setting; receiving via the user interface a user adjudication of the accuracy of the one or more first cardiac event detected in the physiological episode using the first detection setting; displaying on the user interface one or more second cardiac events detected in the same physiological episode using the detection algorithm having a second detection setting that is different than the first detection setting; and updating the detection algorithm to use the second detection setting for detecting cardiac events in subsequent physiological episodes.

The systems, devices, and methods discussed in this document may improve the performance of medical system in detecting a target cardiac event, such as an arrhythmic event, worsening heart failure event, among others. As previously discussed, a challenge in cardiac event detection is repeated FP detections. The present document provides a solution to select or adjust a detection setting using supervised learning from patient prior physiologic event episodes such as those recorded by an AMD. The supervised learning involves user adjudication of the device-generated event episodes. A detection setting corresponding to a desired performance of correctly detecting the target cardiac event from patient prior physiologic event episodes is selected. Because the detection performance is based on a comparison to the user adjudication of the physiologic event episodes, the selected detection setting may help an AMD better recognize subsequent target cardiac event based on the knowledge learned from the prior physiologic event episodes. Compared to conventional cardiac event detection techniques, the supervised learning-based detection setting as discussed herein may reduce FP detection, while preserving the capability of recognizing the TP events, at little to no additional cost or system complexity. With a lower FP rate, inappropriate therapies or medical interventions to the patient may be avoided or reduced, and clinician's time and burden for episode evaluation and adjudication may be lightened. Accordingly, the subject matter discussed herein may better align medical resources to serve those patients with critical medical conditions.

The physiologic event detection and prioritization discussed in this document may also improve the functionality of an AMD, and/or a patient management system. The stored physiologic event episodes may be prioritized for storage in a memory. The event prioritization may be performed in a communicator, a mobile monitor, a programmer, or a remote patient management system in communication with an AMD. As such, in some cases, improved alert management may be achieved without modifying existing patient AMDs or physiologic event detectors. Because only physiologic events with higher priority and/or clinically more relevant to medical diagnosis are stored in the system for clinician review or adjudication, more efficient memory usage may be realized than a traditional medical system. With fewer alerts and events for adjudication, complexity and operating cost of the patient management system can be reduced. Additionally, with reduced FP detections, fewer unnecessary device therapy, drugs, and procedures may be scheduled, prescribed, or provided, battery life and longevity of the AMD can be extended, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting physiologic events in a patient. An embodiment of a medical system includes a memory circuit to store machine-generated physiologic event episodes, such as arrhythmia episodes recorded by an ambulatory medical device. The system can determine a presence of a target cardiac event in one or more of the stored event episodes under a first detection setting, provide the determined presence of the target cardiac event under the first detection setting to a user, and receive an adjudication from the user on the determined presence of the target cardiac event. The control circuit may re-determine (e.g., simulate) a presence of the target cardiac event in the stored physiologic event episodes in the same one or more of the stored event episodes that have previously been analyzed and determined (or one or more different stored event episodes) under a different second detection setting, and provide the re-determined presence of the target cardiac event in the one or more stored physiologic event episodes under the second detection setting to the user. The user can select a detection setting in response to the provided re-determined presence of the target cardiac event in the one or more stored physiologic event episodes. The system can receive the selected detection setting and perform subsequent determinations of the presence of the target cardiac event using the selected detection setting. In an example, a comparison between determinations of the presence of the target cardiac event under the first and second detection settings, or the adjudications and the re-determinations, can be provided to the user. A selected detection setting for a subsequent determination of the presence of the target cardiac event can be received, such as from the user, and the system can program the selected detection setting for the subsequent determination.

Figure 1:
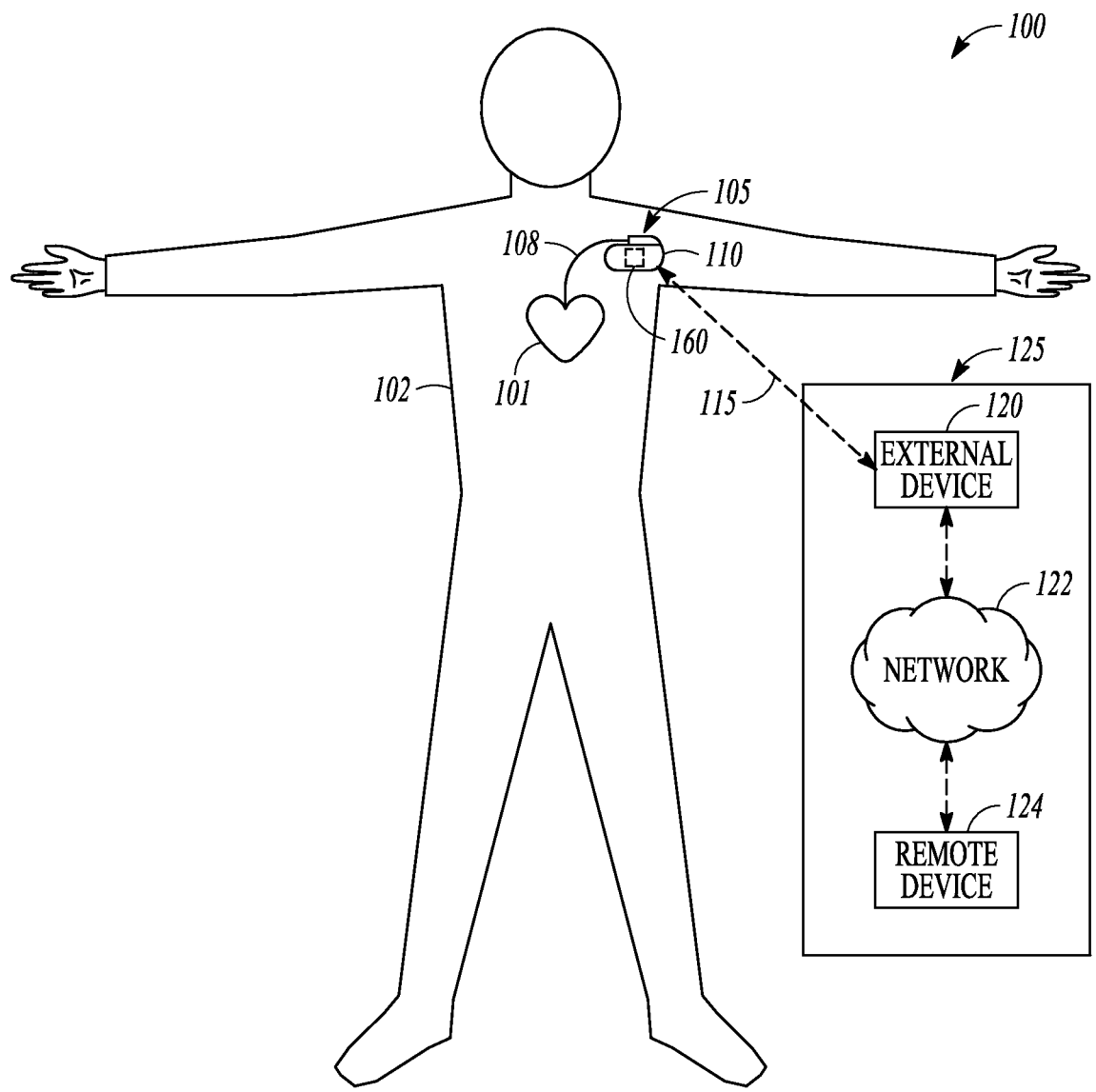
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clink or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a detector circuit 160 to detect a physiologic event using the sensed physiologic signals. In an example, the physiologic event includes a cardiac arrhythmia, such as atrial fibrillation, atrial flutter, atrial tachycardia, supraventricular tachycardia, ventricular tachycardia, or ventricular fibrillation, among other brady- or tachy-arrhythmia. In an example, the detector circuit 160 is configured to detect syncope, a presyncopal event or a precipitating event that may lead to a full-blown syncope. In some examples, the detector circuit 160 is configured to detect worsening of a chronic medical condition, such as worsening heart failure (WHF). The detector circuit 160 may monitor one or more physiologic signals continuously or periodically, and to detect the physiologic event automatically. Additionally or alternatively, the detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a physiologic event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data (e.g., physiologic event episodes) may be collected by the AMD 110, among other data acquisition sensors or devices associated with the patient 102. The remote device 124 may include a storage unit to store the patient data in a patient database. The storage unit may additionally store a plurality of detection settings, such as detection parameters and associated detection criterion (e.g., sensitivity levels, or detection thresholds) or detection algorithms for detecting a presence of a target cardiac event (e.g., an arrhythmia of a particular type) from the stored patient data such as the event episodes detected and recorded by the AMD 110. The server may analyze the device-generated event episodes to determine a presence of a target cardiac event (e.g., a type of cardiac arrhythmia) under a plurality of detection settings, and select a detection setting, from the plurality of detection settings, for detecting subsequent target cardiac event.

In an example, the presence of the target cardiac event can be determined in one or more physiologic event episodes under a first detection setting, such as by the remote device 124. The determined presence of the target cardiac event in the one or more physiologic event episodes can be provided to a user, such as a clinician, for example, using a display. The user can adjudicate the provided determinations, such as using a user interface. In response to the adjudications, the presence of the target cardiac event can be re-determined in the same (or in other examples, different) one or more physiologic event episodes under a second detection setting different than the first detection setting. The re-determined presence of the target cardiac event can be provided to the user, and a selected detection setting (e.g., one of the first or second detection setting, one or more other detection setting, etc.) can be received, such as from the user through the user interface. One or more subsequent determinations can be made using the selected detection setting.

In some examples, the detection setting may be selected using a supervised learning approach, which involves comparing the detected presence of the target cardiac event to a user adjudication of the device-generated event episodes. The detection setting may be selected based on said comparison. The remote device 124 may transmit the selected detection setting to the AMD 110, such as via the communication link 115. The device setting selected based on the supervised learning from patient prior physiologic event episodes may allow the AMD 110 to better detect a subsequent target cardiac event. For example, those cardiac events with similar characteristics to the previously adjudicated FP episode are less likely to be detected; therefore, inappropriate therapies or medical interventions may be avoided. The improved event detection may also reduce the number of episodes to be reviewed and adjudicated by a user.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a physiologic event prioritizer circuit configured to prioritize the alert notifications. For example, an alert of a detected physiologic event may be prioritized using a similarity metric between the physiologic data associated with the detected physiologic event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected physiologic events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the physiologic events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
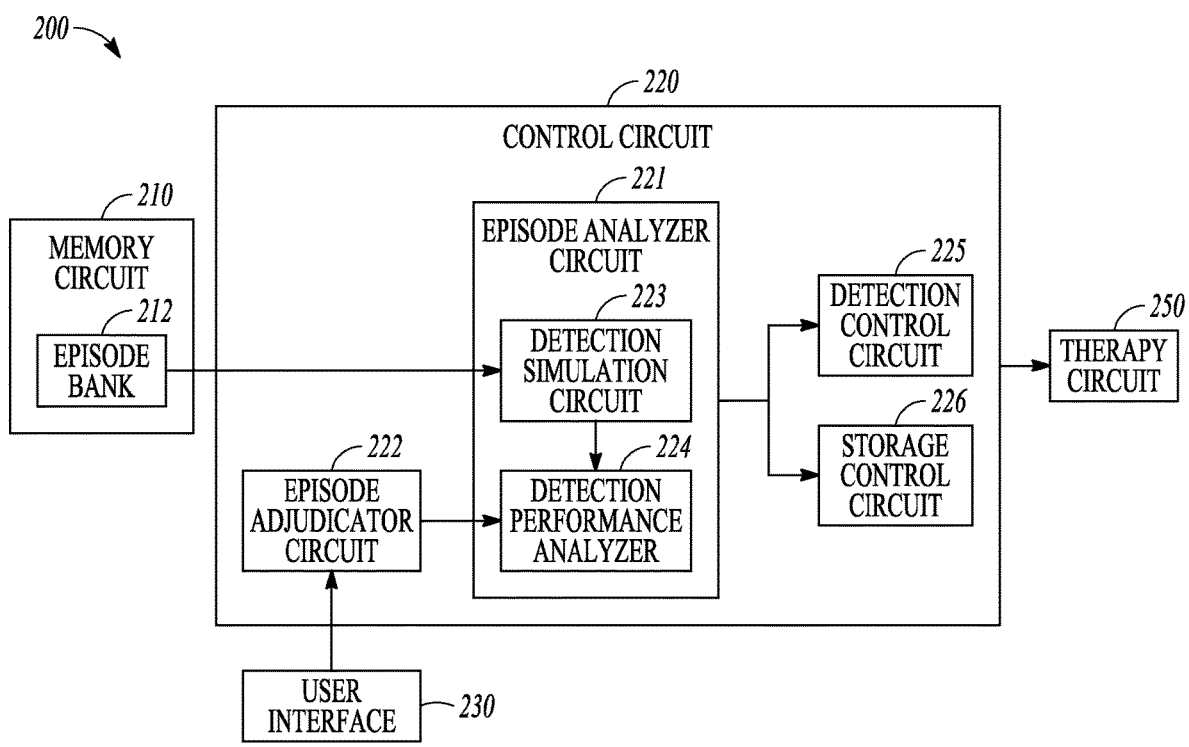
FIG. 2 illustrates generally an example of a physiologic event detection and management system configured to adjust or select a detection setting for detecting a target cardiac event in a patient.

FIG. 2 illustrates generally an example of a physiologic event detection and management system 200 configured to determine or adjust a detection setting for detecting a target cardiac event. Such a detection setting may be programmed into a medical device, such as the AMD 110, to detect subsequent target cardiac event from a patient. The system 200 may prioritize physiologic event episodes detected from a patient, and store said episodes in a memory according to episode priority. At least a portion of the system 200 may be implemented in the external system 125, such as one or more of the external device 120 or the remote device 124, or distributed between the AMD 110 and the external system 125.

The system 200 may include one or more of a memory circuit 210, a control circuit 220, a user interface 230, and an optional therapy circuit 250. The memory circuit 210 may be included in a storage device in the external system 125, such as within the external device 120, or the remote device 124. Alternatively, the memory circuit 210 may be included in an electronic medical record (EMR) system. The memory circuit 210 may store, in an episode bank 212, patient physiologic event episodes such as detected and recorded by the AMD 110. In an example, the memory circuit 210 may be communicatively coupled to the AMD 110, and receive the physiologic event episodes from the AMD 110, such as via the communication link 115, as to be discussed in reference to FIG. 3.

In an example, the physiologic event episodes in the episode bank 212 may include cardiac arrhythmia episodes, such as detected and recorded by the AMD 110. Examples of the cardiac arrhythmia episodes may include atrial arrhythmia episodes, supraventricular arrhythmia episodes, or ventricular arrhythmia episodes, among others. The cardiac arrhythmia episodes may include respective physiologic data sensed from one or more physiologic sensors during the detected arrhythmia event, or additional physiologic data sensed before and/or after the detected arrhythmia event. The physiologic data associated with an arrhythmia episode may include cardiac electrical signals such as one or more electrogram (EGM) signals sensed at various cardiac sites using different electrode combinations, such as one or more atrial EGMs or one or more ventricular EGMs. Additionally or alternatively, the physiologic data may include cardiac mechanical signals or hemodynamic signals such as cardiac pressure signals, impedance signals, heart sounds signals, among others. In various examples, each cardiac arrhythmia episode may additionally include arrhythmia detection or classification generated by a medical device, such as the AMD 110. The arrhythmia detection or classification is a designation of a particular arrhythmia type, such as atrial fibrillation, atrial flutter, ventricular tachycardia, or ventricular fibrillation, among others. Other information about the cardiac arrhythmia episodes such as measurements or signal metrics obtained from the physiologic data (e.g., atrial rate, ventricular rate, variability of atrial or ventricular rate), may also be associated with respective episodes and stored in the episode bank.

In some examples, the episode bank 212 may include patient-triggered episodes, including physiologic data sensed from one or more physiologic sensors in response to a patient trigger, such as when the patient experiences a physiologic event onset. Other information such as patient input about presence of a physiologic event and severity of symptoms, timing information of the symptoms, such as onset and termination time of the patient-triggered episode, may also be associated with the patient-triggered episode and included in the episode bank 212.

Although the discussion of physiologic events management in this document is focused on cardiac arrhythmia episodes, this is meant to be illustrative rather than restrictive in nature or limiting in any way. Episodes of other types of physiologic events, such as syncope, worsening heart failure events, or heart failure decompensation events, may also be stored, analyzed, and provided to a clinician for adjudication using the systems, apparatus, and methods discussed in this document.

The control circuit 220 may be implemented as parts of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The control circuit 220 may include circuit sets comprising one or more other circuits or sub-circuits, including an episode analyzer circuit 221, an episode adjudicator circuit 222, a detection control circuit 225, and a storage control circuit 226. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The episode adjudicator circuit 222 may receive a user input regarding an adjudication of a physiologic event episode such as retrieved from the episode bank 212. Physiologic data collected during the physiologic event episode, and optionally the detection results generated by the AMD, may be displayed on a display unit of the user interface 230. In an example, at least a portion of the user interface 230 may be implemented in the external system 125. A user may provide adjudication through the user interface 230. The adjudication may include a user designation of a cardiac event type in the physiologic event episode. In an example, the adjudication includes a user designation of an arrhythmia type, such as an atrial fibrillation, atrial flutter, supraventricular tachycardia, ventricular tachycardia, or ventricular fibrillation. The episode adjudicator circuit 222 may compare the user designation of arrhythmia type to the detection result generated by the AMD, and identify the episode as a true positive (TP) (or appropriate) detection if the user designation is in agreement with the detection result generated by the AMD, or a false positive (FP) (or inappropriate) detection if the user designation is different from the detection result generated by the AMD. An episode may be identified as indeterminate if no TP or FP decision can be made. Additionally, the user may provide annotations with regard to episode characterization or diagnostic information for the physiologic event episode. For example, when adjudicating a device-detected AF episode, a user (e.g., a clinician) may designate one of a plurality of episode characterizations as a rationale for forming his or her adjudication decision.

The episode analyzer circuit 221 may include a detection simulation circuit 223 configured to analyze physiologic event episodes, such as N episodes $\{X_1, X_2, \ldots, X_N\}$ retrieved from the episode bank 212. The detection simulation circuit 223 may use a detection algorithm to determine, from each of the N episodes $\{X_1, X_2, \ldots, X_N\}$, a presence of a target cardiac event under a set of candidate detection settings $\{S_1, S_2, \ldots, S_M\}$, where M denotes the number of candidate detection settings. The detection algorithm used by the detection simulation circuit 223 may be identical or similar to the detection algorithm used by the AMD for detecting a target cardiac event, such as an arrhythmia detector based on timing or morphology of one or more cardia signals. The candidate detection settings $\{S_1, S_2, \ldots, S_M\}$ may be represented by a plurality of sensitivity levels associated with a specific physiologic parameter. Each sensitivity level may correspond to a detection threshold, or a value range, of the physiologic parameter. For a stored episode $X_k$, the detection simulation circuit 223 determines that a target cardiac event (e.g., an atrial fibrillation event) is present in the episode $X_k$ at detection setting $S_i$ if the physiologic parameter satisfies a condition with respect to $S_i$, such as exceeding a corresponding threshold. The detection simulation circuit 223 determines that the target cardiac event (e.g., an atrial fibrillation event) is absent from the episode $X_k$ at a different detection setting $S_j$ if the physiologic parameter fails to satisfy a condition with respect to $S_j$, such as falling below the corresponding threshold. A lower sensitivity level may correspond to a higher detection threshold, therefore is less sensitive to the target cardiac event. In other words, the target cardiac event is less likely to be detected using a lower sensitivity level than a higher sensitivity level.

The physiologic parameter for determining the presence of the target cardiac event may include a physiologic signal feature, or a composite of multiple signal features, extracted or otherwise measured from a physiologic signal. In an example of cardiac arrhythmia detection, the physiologic parameter may include a temporal feature representing timings of atrial or ventricular events, or a relative timing between atrial and ventricular events, such as a heart rate, a heart rate variability, or an atrioventricular conduction delay, among others. The physiologic parameter may alternatively be a morphological feature representing depolarization pattern of an atrial or a ventricular electrogram. The physiologic parameter may also include a signal feature representing cardiac contractility, which may be extract from a cardiac pressure, impedance, or heart sound signal.

Generally, if a target cardiac event is detected from a particular stored episode (e.g., $X_k$) at a first detection setting $S_i$, the target cardiac event may also be detected at a second, more sensitive, detection setting $S_j$. A more sensitive detection setting may be represented by a higher sensitivity level, or a lower detection threshold. In some examples, the detection simulation circuit 223 may determine a detection setting corresponding to a lowest sensitivity level ($Sens_{LST}$) capable of detecting the target cardiac event in the episode $X_k$. Examples illustrating the $Sens_{LST}$ for a plurality of episodes are discussed below with reference to FIG. 5.

The detection performance analyzer 224 may compare the detection of the target cardiac events from the stored event episodes $\{X_1, X_2, \ldots, X_N\}$ against the user adjudication of the stored event episodes that are provided by the episode adjudicator circuit 222, and determine a detection performance of the detection simulation circuit 223 in recognizing the target cardiac event from the stored event episodes under the candidate detection settings $\{S_1, S_2, \ldots, S_M\}$. In an example, the detection performance may be represented by false positive (FP) counts $\{FP_1, FP_2, \ldots, FP_M\}$ corresponding to the candidate detection settings $\{S_1, S_2, \ldots, S_M\}$. In another example, the detection performance may be represented by FP counts corresponding to the lowest sensitivity levels ($Sens_{LST}$) associated with the stored physiologic event episodes. In yet another example, the detection performance may be represented by a receiver operating characteristic (ROC). The ROC generally depicts detection sensitivity (accuracy of recognizing true positive events) and false positive rate (or specificity) at various operating points. In an example, the operating points may include the candidate detection settings $\{S_1, S_2, \ldots, S_M\}$.

The simulation results generated by the detection simulation circuit 223, such as the presence of a target cardiac event under each of a plurality of candidate detection settings $\{S_1, S_2, \ldots, S_M\}$, along with the physiologic event episodes being analyzed, may be presented to a user (e.g., a clinician) such as via a display unit on the user interface 230. Additionally or alternatively, the detection performance in recognizing the target cardiac event from the stored event episodes under different candidate detection settings, such as generated by the detection performance analyzer 224, may similarly be presented to the user such as displayed on a display unit of the user interface 230. A user may review the physiologic event episodes and the detection performance under different candidate detection settings, and make a selection from the candidate detection settings, or modify an existing detection setting, to detect future physiologic events.

The detection control circuit 225 is configured to select a detection setting S* from the plurality of candidate settings $\{S_1, S_2, \ldots, S_M\}$, such as based on the detection performance. In an example, the detection control circuit 225 selects S* that corresponds to the FP count satisfying a specific condition, such as falling below a FP threshold. In another example, the selected S* corresponds to the least FP count ($FP_{min}$) among the FP counts $\{FP_1, FP_2, \ldots, FP_M\}$ corresponding to the M candidate detection settings $\{S_1, S_2, \ldots, S_M\}$, or the $FP_{min}$ among the FP counts corresponding to the lowest sensitivity levels ($Sens_{LST}$) of the stored physiologic event episodes. In some examples, the selected S* may correspond to the operating point on the ROC that results in a desired compromise between sensitivity and false positive rate. For example, the selected S* may correspond to an operating point that maximizes a sum of sensitivity and specificity, or equivalently a difference between the sensitivity and false positive rate, which is known as the Youden's index. The selected detection setting S* may be programmed to the AMD to detect subsequent target cardiac event from the patient.

In some examples, instead of automatic selection of the detection setting S* from the plurality of candidate settings $\{S_1, S_2, \ldots, S_M\}$, the detection control circuit 225 may receive a user selection of detection setting from the candidate settings. In an example, the detection simulation circuit 223 may perform a simulation to determine a presence of a target cardiac event in the stored physiologic event episodes under a first detection setting $S_1$, and the detection performance analyzer 224 may determine a first detection performance, such as a FP count under the detection setting $S_1$. The determined presence of the target cardiac event under $S_1$ and the first detection performance may be provided to a user (e.g., displayed on a display unit of the user interface 230). The detection control circuit 225 may receive from the user an adjudication of the provided determination of the presence of the target cardiac event under a first detection setting. In response the received adjudication, the detection simulation circuit 223 may re-determine a presence of the target cardiac event in the stored physiologic event episodes under a different second detection setting $S_2$, and the detection performance analyzer 224 may determine a second detection performance, such as a FP count under the detection setting $S_2$. The determined presence of the target cardiac event under $S_2$ and the corresponding detection performance may be provided to the user. A user may make the selection of detection setting, such as between $S_1$ and $S_2$, or among a plurality of settings including $S_1$ and $S_2$. In some examples, the detection control circuit 225 may compare the determinations of the presence of the target cardiac event under $S_1$ and $S_2$, and the first and second detection performances, to the user, such as on a display unit. Based on the comparison, the user may make a selection between the first and second detection settings. The detection control circuit 225 may use the user-selected detection setting to detect a subsequent target cardiac event.

In some examples, the detection settings $\{S_1, S_2, \ldots, S_M\}$ used for detecting the presence of the target event may additionally or alternatively be represented by a plurality of distinct duration thresholds $\{Dur_1, Dur_2, \ldots, Dur_M\}$. The detection simulation circuit 223 determines that a target cardiac event is present in a physiologic event episode (e.g., $X_k$) only if the target cardiac event remains to be detected throughout a time period no shorter than a specific duration threshold (e.g., $Dur_i$). For example, the detection stimulation circuit 223 determines that an AF is present in a stored physiologic event episode only if the physiologic parameter (e.g., a ventricular rate variability) exceeds a sensitivity level for a time period of at least $Dur_i$ seconds. In an example, the duration thresholds $\{Dur_1, Dur_2, \ldots, Dur_M\}$ are distinct and take values approximately between 10-30 seconds. The duration thresholds represent different confidence levels of detecting the target event from a physiologic event episode. For example, if the AF detected in the first stored episode $X_1$ sustains for a duration longer than $Dur_i$ but less than $Dur_j$ (>$Dur_i$), and the AF detected in the second stored episode $X_2$ sustains for a duration longer than $Dur_j$, then a higher confidence of AF detection is attached to the second episode $X_2$ than to the first episode $X_1$.

The automatic detection setting selection or adjustment may be attempted periodically at scheduled time or specific frequency. Alternatively, the automatic detection setting selection or adjustment may be triggered by an event, such as when the adjudication has revealed a substantial number of FP detections from the patient (e.g., exceeding a threshold FP count).

The storage control circuit 226 is configured to prioritize the physiologic event episodes in the memory circuit 210. The episodes may be prioritized based on the $Sens_{LST}$ of the stored event episodes. Generally, $Sens_{LST}$ represents a confidence of detecting the target event from an episode. The lower the $Sens_{LST}$ (e.g., the higher the detection threshold), the higher the confidence of detection of target cardiac event. In an example, a higher priority may be assigned to an event episode if the $Sens_{LST}$ falls below a sensitivity level threshold, and a lower priority may be assigned to an event episode if the $Sens_{LST}$ exceeds the sensitivity level threshold. The storage control circuit 226 may store the high-priority episodes in memory circuit 210 before the low-priority episodes.

The storage control circuit 226 may additionally allocate memory space according to the event priority. In an example, more memory space may be allocated for high-priority episodes than for low-priority episodes. The memory may be dynamically allocated if additional high-priority episodes are generated. For example, the memory space that stores low-priority episodes may be re-allocated for high-priority episodes.

In some examples, the patient physiologic event episodes in the episode bank 212 may be processed before being re-stored in the memory circuit 210. One example of such data processing is data reduction, such as down-sampling operation or digitization of the data samples, to improve the efficiency the memory usage. In an example, a low-priority episode may be reduced at a higher data reduction rate (e.g., using a lower sampling rate and/or a lower resolution) than a high-priority episode. Additionally or alternatively, data reduction may involve data truncation, such that only a selected portion of the episode is stored in the memory 210. In an example, a low-priority episode may be truncated to a shorter duration with less data than a high-priority episode. In an example of priority-based storage of atrial fibrillation (AF) episodes, cardiac data (e.g., EGM data) may be stored for high-priority AF episodes for a longer duration, while only episode characteristic data, such as ventricular rate and AF duration (e.g., AF burden), are stored for low-priority AF episodes.

In addition to prioritizing the pre-existing episodes stored in the episode bank 212, the detection control circuit 225 may prioritize subsequent episodes detected and recorded by the AMD 110 based on their respective $Sens_{LST}$. In an example, a higher priority may be assigned to an episode $X_p$ with a $Sens_{LST}$ at or below a specified sensitivity level threshold, and get stored in the memory 212. A lower priority may be assigned to an episode $X_q$ with the corresponding $Sens_{LST}$ exceeding the specified sensitivity level threshold, with only truncated data (e.g., episode characteristics) get stored in the memory 212. Examples of assigning priority to an episode based on $Sens_{LST}$ are discussed below with reference to FIG. 5.

The prioritization of the stored physiologic event episodes may additionally or alternatively be used in prioritized data transmission. In an example, high-priority episodes may be transmitted between the AMD 110 and the external system 125 before the low-priority episode. In another example, more communication bandwidth may be allocated for transmitting the high-priority episode than the low-priority episodes. Such priority-based control of communication timing, sequence, or bandwidth may help clinicians timely attend to medical events with higher clinical significance or of higher clinical interest, such that proper clinical intervention may be provided as needed. The prioritization of the stored physiologic event episodes may additionally or alternatively be used for prioritized data output, such as presenting the stored physiologic event episodes to a user via the user interface 220. In an example, high-priority episodes may be presented to the user before the low-priority episodes.

The user interface 230 may include a display unit for displaying event episode for adjudication, and a plurality of selectable episode characterizations. Additionally, the display unit may present a recommendation for adjusting AMD programming. The user interface 230 may be coupled to a printer for printing hard copies of the detection information. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the user about the detected physiologic events. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the user about the detected physiologic events. In some examples, the user interface 230 may additionally generate a recommendation for adjusting AMD programming, such as programming to the AMD one or more detection algorithms in the characterization-algorithm association 214.

The optional therapy circuit 250 may be configured to deliver a therapy to the patient in response to the detection of target cardiac event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 250 may modify an existing therapy, such as adjust a stimulation parameter or drug dosage.

Figure 3:
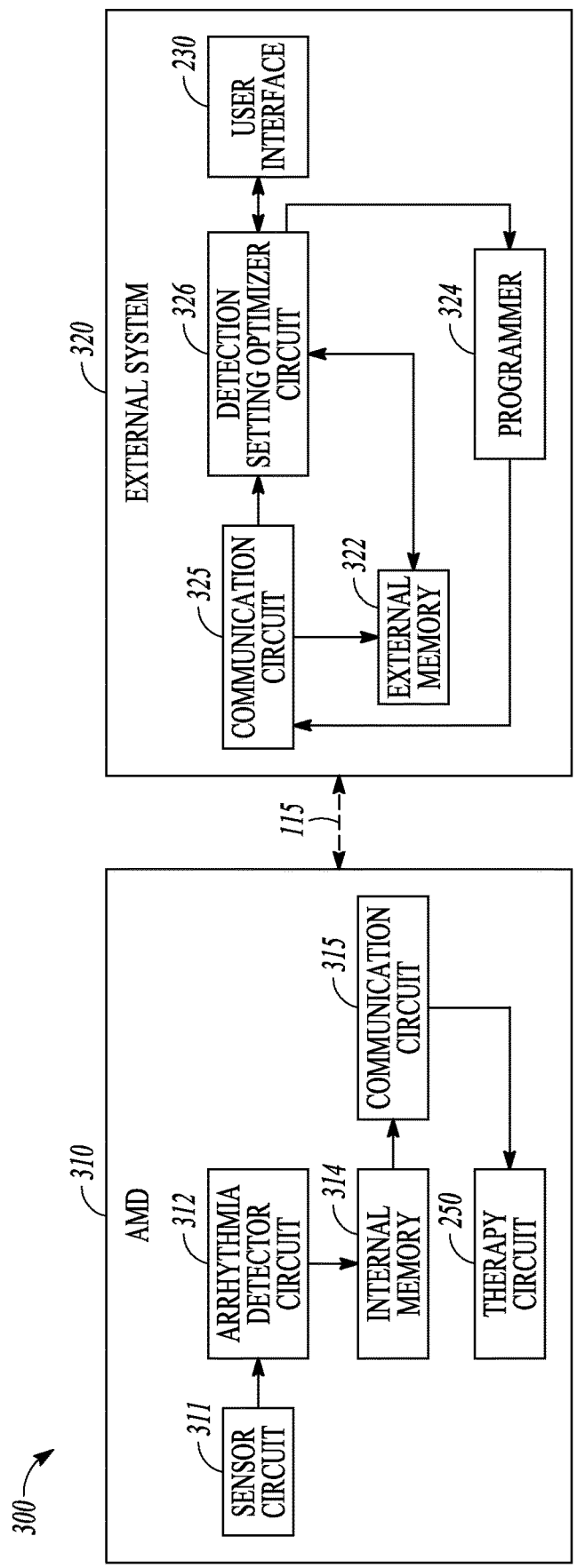
FIG. 3 illustrates generally an example of an arrhythmia management system configured to detect arrhythmia in a patient and manage the detected arrhythmia episodes.

FIG. 3 illustrates generally an example of an arrhythmia management system 300 configured to detect arrhythmia and manage arrhythmia episodes detected from a patient. The arrhythmia management system 300 comprises an AMD 310 and an external system 320, communicatively coupled to each other via the communication link 115.

The AMD 310, which is an embodiment of the AMD 110 illustrated in FIG. 1, may include a sensor circuit 311 for sensing one or more physiologic signals from a subject. The physiologic signals may be sensed via one or more implantable, wearable, or otherwise ambulatory sensors or electrodes associated with the patient. The sensors may be incorporated into, or otherwise associated with an ambulatory device such as the AMD 110. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 311 may include one or more sub-circuits to digitize, filter, or perform other signal conditioning operations on the received physiologic signal. In some examples, the sensor circuit 311 may register a patient-triggered episode. When the patient demonstrates certain signs or symptoms or experiences a precursor event indicative of a target cardiac event, a trigger may be produced and detected by a patient trigger detector. A detection of the patient trigger may activate the sensor circuit 311 to register the patient-triggered episode, and to acquire physiologic data such as one or more physiologic signals.

The arrhythmia detector circuit 312 may be configured to detect a cardiac arrhythmia using the sensed one or more physiologic signals. Examples of the cardiac arrhythmias may include an atrial fibrillation, atrial flutter, supraventricular tachycardia, ventricular tachycardia, or ventricular fibrillation. The detection may be based on timing or morphological features extracted from the one or more physiologic signals. In an example, the arrhythmia detector circuit 312 may detect a specific cardiac arrhythmia using a configurable detection algorithm, such that one or more detection algorithm features may be added or modified via a programming device. The detected arrhythmia episodes, including physiologic data collected during, or additionally before and/or after, the detection, as well as the detection results, may be stored in the internal memory 314.

The communication circuit 315 may transmit the detected arrhythmia episodes (including physiologic data and device-generated detection results) to the external system 320 via the communication link 115. The transmission may be carried out continuously, periodically at scheduled time, or in response to a data interrogation command sent to the AMD 310 from the external system 320. The external system 320, which is an embodiment of the external system 125, may receive the arrhythmia episodes via a communication circuit 325. The external memory 322, which is an embodiment of the memory circuit 210, may store the arrhythmia episodes in the episode bank 212. The external system 320 also includes a detection setting optimizer circuit 326, which is an embodiment of at least a part of the control circuit 220. The detection setting optimizer circuit 326 may perform analysis of the arrhythmia episodes stored in the external memory 322 to detect a presence of a target arrhythmia type (e.g., AF) using an arrhythmia detection algorithm such as the one used by the arrhythmia detector circuit 312 in the AMD 310. The detection of target arrhythmia may be performed using a plurality of candidate detection settings, such as distinct sensitivity levels. The external system 320 includes the user interface 230 that enables a user to annotate the stored arrhythmia episodes, including providing adjudication decisions. The detection setting optimizer circuit 326 may select from the candidate detection settings a detection setting corresponding to a desired detection performance, such as number of false positive (FP) detections in the stored arrhythmia episodes. The detection setting optimizer circuit 326 may also assign priorities to the arrhythmia episodes, such as based on the $Sens_{LST}$ associated with each arrhythmia episode, as discussed above, and prioritize the arrhythmia episodes. The stored arrhythmia episodes may be presented to a user for evaluation and adjudication, such as via the user interface 230, in an order according to the episode priorities.

The external system 320 includes a programmer 324 that may generate commands for programming the AMD 310 with the selected detection setting, among other event sensing, arrhythmia detection, or data collection commands. In an example, the selected detection setting may be confirmed or otherwise modified by a user via the user interface 230, and forwarded to the AMD 310 via the communication link 115. The AMD 310 may detect a target arrhythmia using the selected detection setting, record the arrhythmia episode, and transmit the arrhythmia episode to the external system via the communication link 115.

Figure 4:
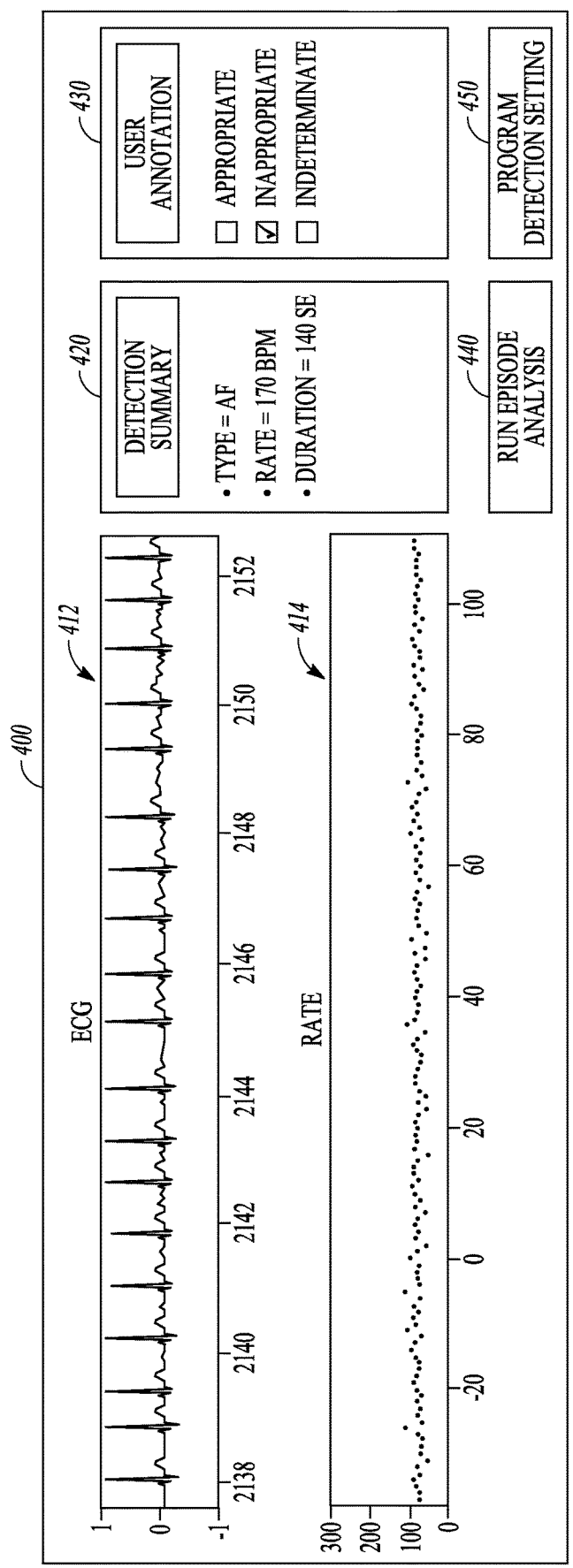
FIG. 4 illustrates an example of a of a user interface for displaying physiologic event episodes, receiving user adjudication of the physiologic event episodes and interactive programming of detection setting.

FIG. 4 illustrates an example of at least a portion of a user interface 400 for displaying physiologic event episodes, receiving user adjudication of the physiologic event episodes and interactive programming of detection setting. The user interface portion 400, which is an embodiment of the display unit of the user interface 230, includes a display of information of a physiologic event episode generated by a medical device, such as the AMD 310. By way of example and not limitation, the information may include physiologic data 412 and a trend of measurements 414 taken from the physiologic data 412. Information about the patient identification and episode number may also be displayed, and may be selected such as using drop-down lists, check boxes, radio buttons, list boxes, buttons, toggles, text fields, among other input control elements on the user interface 400. The physiologic data 412 may be sensed using electrodes or physiologic sensors in communication with the medical device, and collected during, or alternatively before or after, the detected physiologic event. By way of non-limiting example as illustrated in FIG. 4, the physiologic data 412 includes an electrogram sensed at a cardiac site, such as a ventricle. In some examples, two or more physiologic signals may be displayed, including EGMs from multiple cardiac sites or via different sensing electrode configurations, cardiac mechanical signals, or hemodynamic signals sensed from one or more sensors. The trend of measurements 414 may include within-channel or inter-channel timing information, such as a heart rate trend, a heart rate variability trend, or an atrioventricular interval trend. The displayed information may include a detection summary 420. By way of example, the detection summary 420 may include a physiologic event type detected by the AMD, and measurements from the sensed physiologic signals as taken by the AMD. In the example illustrated in FIG. 4, the displayed episode is detected as an AF episode having a ventricular rate of 170 bpm and a duration of 140 seconds.

The user interface portion 400 may include a display zone to receive user annotation of the displayed episode, such as an adjudication of an event type (e.g., a particular arrhythmia type), or a designation of appropriate (e.g., true positive) detection indicating a user agreement with the device-detected arrhythmia type, or inappropriate (e.g., false positive) detection indicating a user disagreement with the device-detected arrhythmia type.

The user interface portion 400 may include one or more of input control elements (e.g., an on-screen buttons) allowing a user to run episode analysis 440, and to program detection setting 450. When the run episode analysis 440 is activated, the episode analyzer circuit 221 may analyze the physiologic event episodes stored in the episode bank 212. A detection performance under a plurality of candidate detection settings, such as sensitivity levels and/or duration thresholds, may be displayed on the user interface 400. Examples of episode analysis and a presentation of analysis results are discussed below with reference to FIG. 5. When the program detection setting 450 is activated, a detection setting may be selected, or an existing detection setting in the AMD may be adjusted, and programmed into the AMD. In an example, a user (e.g., a clinician) may manually select or adjust the detecting setting based on the analysis of the patient physiologic event episodes. Alternatively, the detection control circuit 225 may automatically select or adjust a detection setting selection based on a detection performance, such as FP counts under the plurality of candidate detection settings, or an ROC, as previously discussed with reference to FIG. 2. The user may confirm or modify the automatic selection of detection setting.

Figure 5:
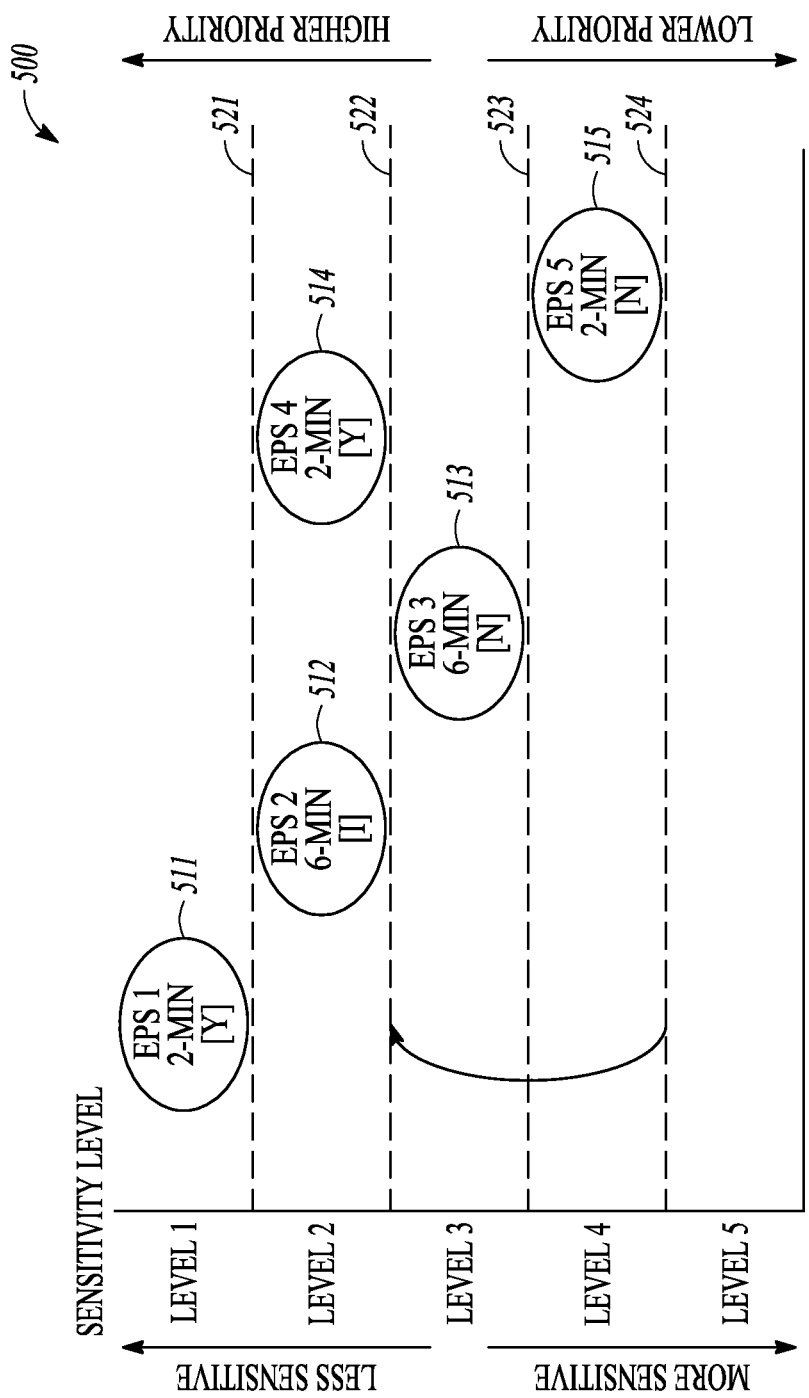
FIG. 5 is a diagram illustrating an example of selecting or adjusting an arrhythmia detection setting based on analysis of device-detected arrhythmia episodes stored in the memory.

FIG. 5 is a diagram 500 illustrating an example of selecting or adjusting an arrhythmia detection setting based on analysis of device-detected arrhythmia episodes stored in the memory. By way of example, five episodes 511-515 recorded by an AMD from a patient are each analyzed by the episode analyzer circuit 221 to determine whether atrial fibrillation (AF) is present in the corresponding episode under each of five different detection settings. The episode analyzer circuit 221 may use an AF detection algorithm identical or similar to that used by the AMD. The detection algorithm includes a comparison of measurements of physiologic parameter taken from an episode against a sensitivity level. The physiologic parameter for detecting AF may include a ventricular heart rate threshold, a ventricular heart rate variability threshold, among others.

The five distinct detection settings are represented respectively by sensitivity levels 1-5, corresponding to detection thresholds 521-525 for the specific physiologic parameter. A higher sensitivity level corresponds to a lower detection threshold, with which an AF event is more likely to be detected. As illustrated in FIG. 5, sensitivity level 1<level 2<level 3<level 4<level 5; and the corresponding threshold 521>threshold 522>threshold 523>threshold 524. An AF is determined to be present in a stored episode under a particular sensitivity level (e.g., level 3) if the physiologic parameter falls within a value range (e.g., between thresholds 522 and 523, for sensitivity level 3).

A lowest sensitivity level ($Sens_{LST}$) capable of detecting the AF may be determined for each of the episodes 511-515, such as using the episode analyzer circuit 221. For example, because AF is detected in episode 513 under sensitivity levels 3, 4 and 5, the $Sens_{LST}$ for episode 513 is level 3 (the lowest among the levels 3, 4, and 5). The episode analyzer circuit 221 may similarly determine the $Sense_{LST}$ of level 1 for episode 511, level 2 for episode 512, level 2 for episode 4, and level 4 for episode 5, etc.

Each of the episodes 511-515 may be adjudicated, such as using the episode adjudicator circuit 222, as one of an appropriate AF detection marked as a "Y" episode (i.e., a true positive or TP detections), an inappropriate AF detection marked as an "N" episode (i.e., false positive or FP detections), or an un-adjudicated or indeterminate episode marked as an "I" episode. The detection control circuit 225 may select or adjust the detection setting using the lowest sensitivity levels ($Sense_{LST}$) of the stored episodes and the adjudication. The selection may be based on a detection performance, such as FP counts corresponding to the plurality of candidate settings or the $Sense_{LST}$ of the physiologic event episodes, or an ROC or a measure taken therefrom, as discussed above with reference to FIG. 2. For example, the detection control circuit 225 may recommend adjusting the sensitivity level 4 (which corresponds to detection threshold 524 as currently being used by the AMD) to a lower sensitivity level 2 (which corresponds to detection threshold 522). Because level 2 is less sensitive than level 4, the AMD would have avoided the FP detections of episodes 513 and 515. Programming the new sensitivity level 2 to the AMD may prospectively reduce future FP detections, such as events having similar characteristics to episodes 513 or 515. In an example, the adjusted or selected detecting setting, along with the detection performance, may be displayed to a user, who can confirm or modify the automatically determined detection setting. Alternatively, a user may manually select or adjust the detection setting (e.g., sensitivity level or the detection threshold).

As illustrated in FIG. 5, each of the episodes 511-515 may also be annotated with respective duration (e.g., 2 minutes). The episode analyzer circuit 221 may determine a presence of AF in each episode under the plurality of duration thresholds $\{Dur_1, Dur_2, \ldots, Dur_M\}$. AF is determined to be present in a stored episode under a specific sensitivity level only if the physiologic parameter satisfies the condition with respect to said sensitivity level throughout a time period no shorter than a duration threshold.

The storage control circuit 226 may determine the priority for storing the episodes 511-515 in the memory. As discussed above with reference to FIG. 2, episodes with a lower $Sens_{LST}$ has a higher priority to be stored in the memory. Episodes 511, 512 and 514 have their $Sens_{LST}$ at lower levels 1 and 2, and are each assigned a higher priority. Episodes 513 and 515 each have $Sense_{LST}$ at higher sensitivity levels 3 and 4, and therefore are each assigned a lower priority. High-priority episodes 511, 512 and 514 may have more data to be stored in the memory with larger space allocation, while the low-priority episodes 513 and 515 are not stored in the memory, or have less data (e.g., only the episode characteristics) to be stored in the memory.

Figure 6:
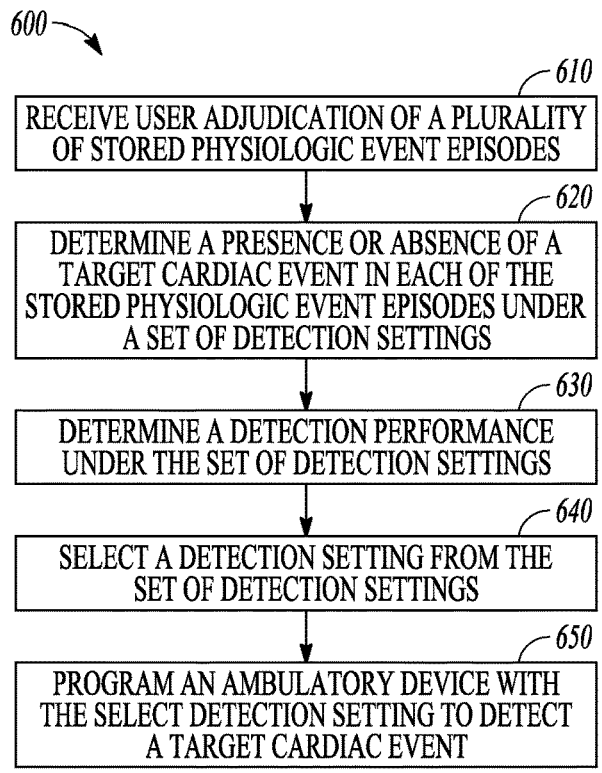
FIG. 6 is a flowchart illustrating an example of a method of selecting or adjusting an arrhythmia detection setting to detect a target cardiac event.

FIG. 6 is a flowchart illustrating an example of a method 600 of selecting or adjusting an arrhythmia detection setting to detect a target cardiac event in a patient. Examples of the physiologic events include cardiac arrhythmia, such as atrial fibrillation, atrial flutter, atrial tachycardia, supraventricular tachycardia, ventricular tachycardia, or ventricular fibrillation, among other brady- or tachy-arrhythmia. The method 600 may be implemented and executed in an ambulatory medical device such as an implantable or wearable medical device, or in a remote patient management system. In an example, the method 600 may be implemented in, and executed by, the AMD 110, one or more devices in the external system 125, or the physiologic event detection and management system 200. Although the present document is focused on cardiac arrhythmia detection, the system and methods discussed herein, or variations thereof, may be used to detect and manage other physiologic events, such as syncope, presyncope, or a chronic medical condition such as a worsening heart failure (WHF) event.

The method 600 commences at 610, where a user adjudication of a plurality of physiologic event episodes, such as cardiac arrhythmia episodes detected and recorded by the AMD 110, may be received. The cardiac arrhythmia episodes may each include physiologic data sensed from one or more physiologic sensors during the detected arrhythmia event, or additionally physiologic data sensed before and/or after the detected arrhythmia event, and may be stored in an episode bank 212. The physiologic data associated with an arrhythmia episode may include cardiac electrical or mechanical signals or hemodynamic signals such as cardiac pressure signals, impedance signals, heart sounds signals, among others. Other information about the cardiac arrhythmia episodes, such as measurements or signal metrics obtained from the physiologic data (e.g., atrial rate, ventricular rate, variability of atrial or ventricular rate), and device-generated arrhythmia detection or classification decision associated with each arrhythmia episode, may also be received at 610. The arrhythmia detection or classification is a designation of a particular arrhythmia type, such as atrial fibrillation, atrial flutter, ventricular tachycardia, or ventricular fibrillation, among others.

The information of the cardiac arrhythmia episodes may be presented to a user (e.g., a clinician), such as displayed on a screen of the user interface 230. The user may provide adjudication using, for example, the input control elements such as displayed on illustrated in FIG. 4. The adjudication may include a user designation of presence of a specific physiologic event, such as an arrhythmia type (e.g., atrial fibrillation, atrial flutter, supraventricular tachycardia, ventricular tachycardia, or ventricular fibrillation). In some examples, the adjudication may include a designation of a TP decision (indicating an agreement between adjudication decision and the detection result generated by the AMD) or as a FP decision (indicating a disagreement between adjudication decision and the detection result generated by the AMD). An episode may be designated as indeterminate if decision on arrhythmia type, or TP or FP decision, cannot be made. In some examples, the adjudication may include episode characterization or diagnostic information.

At 620, the physiologic event episodes may be analyzed to determine, for each of the stored physiologic event episodes, a presence of a target cardiac event under a set of candidate detection settings, such as using the episode analyzer circuit 221. A target cardiac event is determined to be present in a received physiologic event episode $X_k$ at a detection setting $S_i$ if the physiologic parameter satisfies a condition (e.g., exceeding a threshold). A target cardiac event is determined to be absent from the episode $X_k$ at a different detection setting $S_j$ if the physiologic parameter fails to satisfy a condition, such as falling below the corresponding threshold. The detection algorithm used to determine the presence of the target cardiac event at 620 may be identical or similar to the detection algorithm used by the AMD for detecting and recording the physiologic event episodes, such as an arrhythmia detector based on timing or morphology of cardia signals sensed from one or more cardiac sites. The candidate detection settings may be represented by a plurality of sensitivity levels for a specific physiologic parameter. Each sensitivity level may correspond to a detection threshold, or a value range of the physiologic parameter. The physiologic parameter for determining the presence of the target cardiac event may include a physiologic signal feature, such as temporal feature or a morphologic feature, extracted or otherwise measured from a physiologic signal, or a composite of multiple signal features.

The candidate detection settings may additionally or alternatively be represented by a plurality of duration thresholds. A target cardiac event is determined to be present in a stored episode only if the target cardiac event remains to be detected throughout a time period no shorter than a specific duration threshold. In an example of detecting an arrhythmia from a stored episode, a detection corresponding to a longer duration threshold suggests that the detected arrhythmia lasts for a longer duration, and therefore is more likely a true arrhythmia event, than a detection corresponding to a shorter duration threshold.

At 630, a detection performance of detecting the target cardiac event from the physiologic event episodes under the candidate detection settings may be determined, such as using a comparison of the detection results on the physiologic event episodes at 620 against the user adjudication of the physiologic event episodes at 610. The detection performance may be represented by false positive (FP) counts corresponding to the candidate detection settings, or a receiver operating characteristic (ROC) that depicts the detection sensitivity and false positive rate at various operating points as represented by the candidate detection settings.

At 640, a detection setting may be selected from the candidate detection settings based on the determined performance. In an example, the selected detection setting corresponds to the FP count satisfying a specific condition, such as falling below a FP threshold. In another example, the selected detection setting corresponds to the least FP count (FPmin) among the candidate detection settings. In yet another example, the selected detection setting may be determined as the operating point on the ROC curve that corresponds to a desired comprise between sensitivity and false positive rate, such as one that maximizes the difference between the sensitivity and false positive rate.

At 650, the selected detection setting may be programmed to an AMD, either automatically or upon a user confirmation, to detect subsequent target cardiac event from the patient. The automatic detection setting selection or adjustment may be attempted periodically at scheduled time or specific frequency. Alternatively, the automatic detection setting selection or adjustment may be triggered by an event, such as when the adjudication has revealed a substantial number of FP detections from the patient (e.g., exceeding a threshold FP count).

Figure 7:
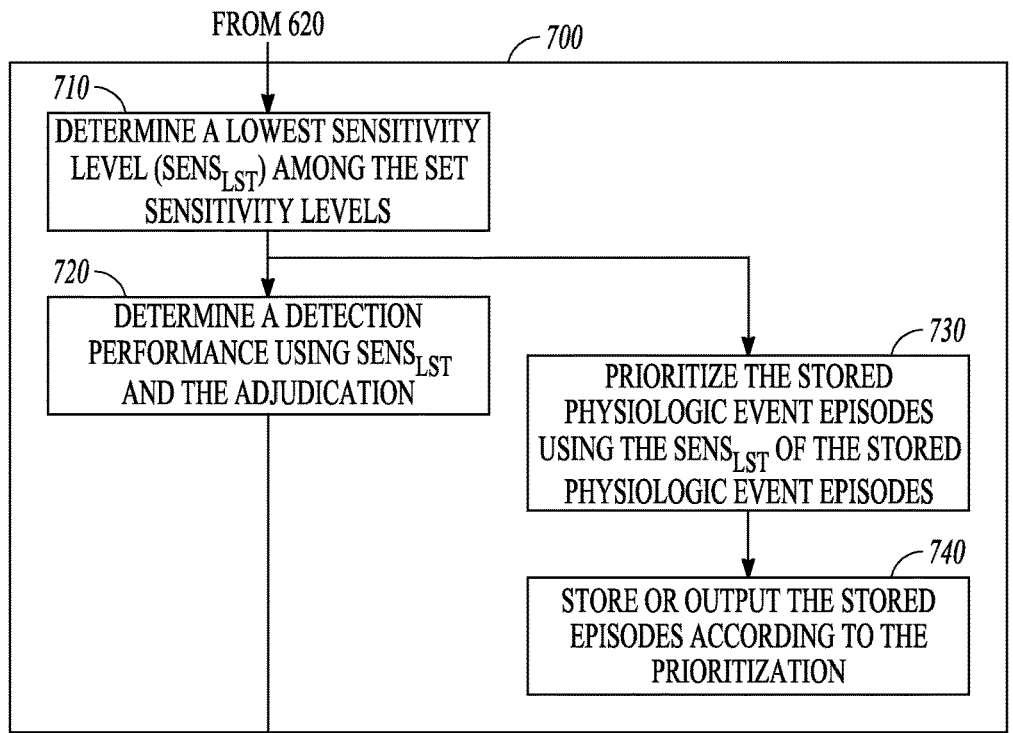
FIG. 7 is a flowchart illustrating an example of a portion of a method of determining a performance for detecting a target cardiac event from physiologic event episodes and prioritizing the physiologic event episodes for storage in a memory.

FIG. 7 is a flowchart illustrating an example of a portion of a method 700 of determining a performance for detecting a target cardiac event from physiologic event episodes, and prioritizing the physiologic event episodes for storage in a memory. The method 700 may represent an embodiment of a portion of the algorithm 600, such as step 630.

At 710, the detection results on the stored physiologic event episodes obtained at 620 may be used to determine a lowest sensitivity level ($Sens_{LST}$) among the sensitivity levels corresponding to the set of candidate detection settings under which the target cardiac event may be detected from the physiologic event episode. $Sens_{LST}$ represents a confidence of detecting the target event from an episode. The lower the $Sens_{LST}$ (e.g., the higher the detection threshold), the higher the confidence of detection of target cardiac event.

At 720, a detection performance may be determined using the $Sens_{LST}$ of the physiologic event episodes and the adjudication. Examples of the detection performance may include FP counts corresponding to the lowest sensitivity levels ($Sens_{LST}$) of the stored physiologic event episodes. A detection setting may then be selected at 640 corresponding to the FPmin among the FP counts corresponding to the $Sens_{LST}$ of the stored physiologic event episodes.

The $Sens_{LST}$ determined at 710 may be used to prioritize the physiologic event episodes at 730, such as the pre-existing episodes stored in the episode bank 212, as well as subsequent episodes recorded by an AMD. Episode prioritization may be performed, for example, using the storage control circuit 226. A higher priority may be assigned to an event episode if the $Sens_{LST}$ falls below a sensitivity level threshold, and a lower priority may be assigned to an event episode if the $Sens_{LST}$ exceeds the sensitivity level threshold.

At 740, the physiologic event episodes may be stored in a memory (such as the episode bank 212) according to their respective priorities. High-priority episodes may be stored in a memory circuit before the low-priority episodes. More memory space may be allocated for high-priority episodes than for low-priority episodes. In an example, when additional high-priority episodes are provided (such as detected and recorded by the AMD), the memory space that stores low-priority episodes may be re-allocated for high-priority episodes.

The priorities of the physiologic event episodes may also be used to determine an amount of information of the physiologic event episodes to be stored in the memory. In various examples, to improve efficiency of memory usage, data reduction may be performed on the physiologic event episodes before they are stored in the memory. Data reduction may be achieved using a low sampling rate or a low data resolution, or data truncation with only a selected portion of the episode is stored in the memory. In an example, low-priority episodes may be reduced at a higher data reduction rate, such as a lower sampling rate or a lower resolution, than the high-priority episodes. In another example, low-priority episodes may be truncated to a shorter duration than a high-priority episode. In an example of prioritizing AF episodes, cardiac data (e.g., EGMs) collected during the AF may be stored for high-priority AF episodes for a longer duration, while for low-priority AF episodes only episode characteristic data, such as ventricular rate and AF duration (AF burden), are stored in the memory.

In addition to priority-based data storage, the prioritization of the stored physiologic event episodes may additionally or alternatively be used for scheduling data transmission at 740, such as timing, order, or bandwidth allocation for transmitting the physiologic event episode from one device to another. For example, high-priority episodes may be transmitted from the AMD 110 to the external system 125 before the low-priority episode. More communication bandwidth may be allocated for transmitting high-priority episodes than low-priority episodes. The physiologic event episodes may be output to a user in accordance with the prioritization of the stored physiologic event episodes. In an example, high-priority episodes may be presented to the user before the low-priority episodes.

Figure 8:
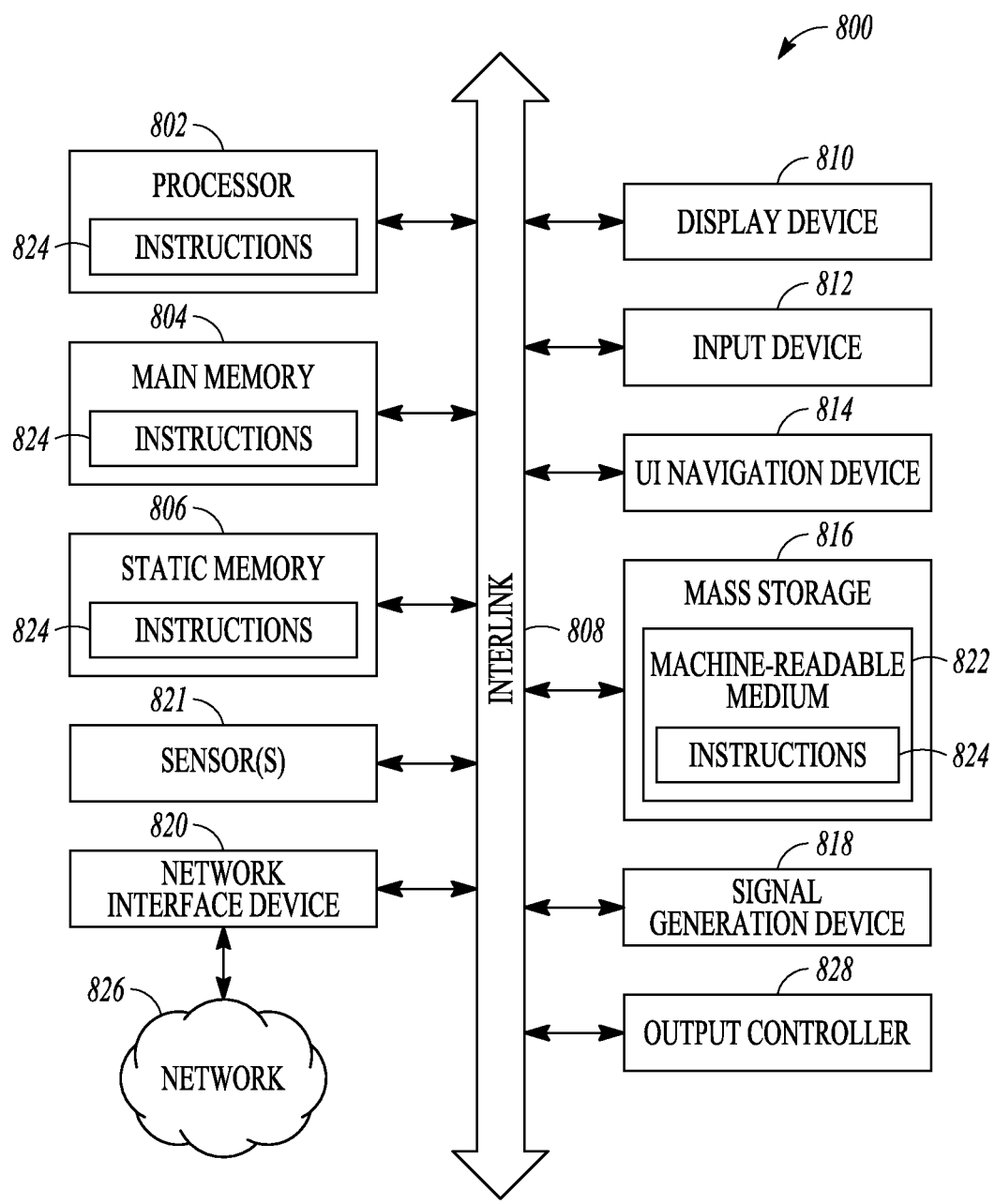
FIG. 8 is a block diagram illustrating generally an example machine upon which any one or more of the techniques (e.g., methodologies) discussed herein may perform.

FIG. 8 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine-readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communication network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communication network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for detecting cardiac events from a patient, the system comprising:
   a memory circuit configured to store physiologic event episodes recorded by a medical device from the patient that satisfy a first detection setting of the medical device; and
   a control circuit, including a detection control circuit configured to perform offline analysis of the stored physiologic event episodes to determine a presence of a target cardiac event under a second detection setting having a different detection parameter value than the first detection setting of the medical device, comprising to:
   display, on one user interface, the determined presence of the target cardiac event of a first event episode under the first detection setting to a user;
   receive from the user an adjudication of the target cardiac event of the first event episode under the first detection setting;
   determine an indication that the first event episode is a false positive (FP) event episode under the first detection setting based on the received adjudication of the target cardiac event of the first event episode;
   in response to the determined indication that the first event episode is a FP event episode, re-determine a presence of the target cardiac event for the stored physiologic event episodes that satisfy the second detection setting; and
   present information about the re-determined presence of the target cardiac event for the stored physiologic event episodes under the first and second detection settings to reduce an adjudication burden of the user.

2. The system of claim 1, wherein the stored event episodes occur in the patient at different times than the first event, where the control circuit is configured to program the medical device with the second detection setting to detect future event episodes of the target cardiac event in the patient.

3. The system of claim 1, wherein the detection control circuit is configured to determine a receiver operating characteristic (ROC) with operating points including the first and second detection settings, and to provide the determined ROC to the user.

4. The system of claim 1, wherein the first and second detection settings include respective first and second sensitivity levels, and wherein, to determine the presence of the target cardiac event in one of the stored physiologic event episodes, the detection control circuit is configured to compare a physiologic parameter derived from the one of the stored physiologic event episodes to the first and second sensitivity levels.

5. The system of claim 4, wherein the detection control circuit is further configured to:
   determine, for each of the stored physiologic event episodes, a lowest sensitivity level ($Sens_{LST}$) among a plurality of sensitivity levels including the first and second sensitivity levels that are capable of detecting the presence of the target cardiac event from the corresponding stored physiologic event episode; and
   select a detection setting from the plurality of sensitivity levels using the $Sens_{LST}$ of the stored physiologic event episodes.

6. The system of claim 1, wherein the first and second detection settings include respective first and second duration thresholds, and wherein, to determine the presence of the target cardiac event in one of the stored physiologic event episodes, the detection control circuit is configured to compare a duration of the one of the stored physiologic event episodes to the first and second duration thresholds.

7. The system of claim 1, comprising a user interface configured to receive a user input of the adjudication of the target cardiac event of the first event episode,
   wherein the detection control circuit is configured to receive, based on the determined presence of the target cardiac event under the first and second detection settings, a user selected detection setting,
   wherein the control circuit is configured to program the medical device with the user selected detection setting to detect future episodes of the target cardiac event in the patient.

8. The system of claim 5, wherein the control circuit further includes a storage control circuit configured to prioritize the stored physiologic event episodes based on the $Sens_{LST}$ of the stored physiologic event episodes.

9. The system of claim 8, wherein the storage control circuit is configured to store a first number of data features of the event episode if a high priority is assigned, and to store a second, lower number of data features of the event episode if a low priority is assigned.

10. A method for detecting cardiac events from a patient, the method comprising:
    storing in a memory physiologic event episodes recorded by a medical device from the patient that satisfy a first detection setting of the medical device;
    performing offline analysis, using a control circuit, of the stored physiologic event episodes to determine a presence of a target cardiac event under a second detection setting having a different detection parameter value than the first detection setting, the offline analysis including;
    displaying, on one user interface, the determined presence of the target cardiac event of a first event episode under the first detection setting to a user;
    receiving from the user an adjudication of the target cardiac event of the first event episode under the first detection setting;
    determining an indication that the first event episode is a false positive (FP) event episode under the first detection setting based on the received adjudication of the target cardiac event of the first event episode;
    in response to the determined indication that the first event episode is a FP event episode, re-determining a presence of the target cardiac event for the stored physiologic event episodes that satisfy a second detection setting different than the first detection setting; and
    presenting information about the re-determined presence of the target cardiac event for the stored physiologic event episodes under the first and second detection settings to reduce an adjudication burden of the user.

11. The method of claim 10, wherein the stored event episodes occur in the patient at different times than the first event, the method further comprising programming the medical device with the second detection setting to detect future event episodes of the target cardiac event in the patient.

12. The method of claim 10, comprising determining a receiver operating characteristic (ROC) with operating points including the first and second detection settings, and providing the determined ROC to the user.

13. The method of claim 10, wherein the first and second detection settings include respective first and second sensitivity levels, and wherein determining the presence of the target cardiac event in a stored physiologic event episode includes using a comparison of a physiologic parameter derived from the stored physiologic event episode to the first and second sensitivity levels.

14. The method of claim 13, comprising determining, for each of the stored physiologic event episodes, a lowest sensitivity level ($Sens_{LST}$) among a plurality of sensitivity levels including the first and second sensitivity levels that are capable of detecting the presence of the target cardiac event from the corresponding stored physiologic event episode, and selecting a detection setting from the plurality of sensitivity levels using the $Sens_{LST}$ of the stored physiologic event episodes.

15. The method of claim 14, comprising prioritizing the stored physiologic event episodes based on the $Sens_{LST}$ of the stored physiologic event episodes using a storage control circuit.

16. The method of claim 10, wherein the first and second detection settings include respective first and second duration thresholds, and wherein determining the presence of the target cardiac event in a stored physiologic event episode includes using a comparison of a duration of the stored physiologic event episode to the first and second duration thresholds.

17. A system for detecting cardiac events from a patient, comprising:
    a medical device configured to detect from the patient, and store in a memory, a plurality of event episodes including first stored event episodes indicative of a determined presence of a target cardiac event under a first detection setting; and
    a control circuit configured to:
        provide a first event under the first detection setting to a user for adjudication;
        receive from the user a user adjudication of the first event under the first detection setting;
        determine a false positive (FP) indication for the first event based on a comparison of the received user adjudication to the determined presence of the target cardiac event under the first detection setting;
        in response to the determined FP indication for the first event, re-determine a presence of the target cardiac event for the first stored event episodes under a second detection setting having a different detection parameter value than the first detection setting;
        provide second stored event episodes recorded by the medical device from the patient under the second detection setting, the second stored event episodes fewer than the first stored event episodes; and
        provide information about the re-determined presence of the target cardiac events for the second stored event episodes under the second detection setting to the user to reduce an adjudication burden of the user.

18. The system of claim 17, wherein the first and second detection settings each include respective first and second sensitivity levels, and wherein to determine the presence of the target cardiac event in one of the first stored event episodes, the detection control circuit is configured to compare a physiologic parameter derived from the one of the stored physiologic event episodes to the first and second sensitivity levels.

19. The system of claim 17, wherein the first and second detection settings each include respective first and second duration thresholds, and wherein, to determine the presence of the target cardiac event in one of the first stored event episodes, the detection control circuit is configured to compare a duration of the one of the first stored event episodes to the first and second duration thresholds.

20. The system of claim 17, wherein the stored event episodes occur in the patient at different times than the first event, wherein the control circuit is configured to program the medical device with the second detection setting to detect future event episodes of the target cardiac event in the patient.

* * * * *